United States Patent
Dieras et al.

(10) Patent No.: US 7,927,557 B2
(45) Date of Patent: Apr. 19, 2011

(54) POST-DISCHARGE PLASMA STERILISATION DEVICE AND METHOD

(75) Inventors: Francis Dieras, Bordeaux (FR); André Ricard, Toulouse (FR); Michel Sixou, Balma (FR); Sandrine Villeger, Toulouse (FR)

(73) Assignee: Societe pour la Conception des Applications des Techniques Electroniques-SATELEC, Merignac (FR)

( * ) Notice: Subject to any disclaimer, the term of this patent is extended or adjusted under 35 U.S.C. 154(b) by 1146 days.

(21) Appl. No.: 10/560,243

(22) PCT Filed: Jun. 28, 2004

(86) PCT No.: PCT/FR2004/001640
§ 371 (c)(1),
(2), (4) Date: Apr. 19, 2006

(87) PCT Pub. No.: WO2005/000366
PCT Pub. Date: Jan. 6, 2005

(65) Prior Publication Data
US 2007/0092397 A1    Apr. 26, 2007

(30) Foreign Application Priority Data
Jun. 27, 2003 (FR) .................................. 03 07799

(51) Int. Cl.
*A61L 2/00* (2006.01)
(52) U.S. Cl. ............... 422/292; 422/22; 422/23; 422/28; 422/305; 204/164

(58) Field of Classification Search .................... 422/22, 422/23, 28, 186, 292, 305; 204/164
See application file for complete search history.

(56) References Cited

U.S. PATENT DOCUMENTS

| | | | |
|---|---|---|---|
| 3,948,601 A | | 4/1976 | Fraser et al. |
| 5,178,829 A | * | 1/1993 | Moulton et al. ................ 422/23 |
| 5,667,753 A | * | 9/1997 | Jacobs et al. ................... 422/29 |
| 5,741,460 A | * | 4/1998 | Jacob et al. ..................... 422/22 |
| 6,096,564 A | * | 8/2000 | Denes et al. ..................... 438/1 |
| 6,467,618 B2 | * | 10/2002 | High et al. .................... 206/370 |

FOREIGN PATENT DOCUMENTS

| | | |
|---|---|---|
| DE | 197 15 583 | 10/1998 |
| EP | 0 377 799 | 7/1990 |
| FR | 2 759 590 | 8/1998 |
| FR | 2 790 962 | 9/2000 |
| FR | 2 814 079 | 3/2002 |
| FR | 2 821 557 | 9/2002 |
| WO | WO 03/043666 | 5/2003 |
| WO | WO 2004/016291 | 2/2004 |
| WO | WO 2004/050128 | 6/2004 |

* cited by examiner

Primary Examiner — Sean E Conley
(74) Attorney, Agent, or Firm — Young & Thompson

(57) ABSTRACT

A device used for the sterilization of objects (19), in particular medical or surgical instruments, is of the type that can create a gaseous plasma from a gas flow which is subjected to an electric field. The resulting post-discharge flow is brought into contact with the surface of the objects to be treated. The device is characterized in that the gas flow includes exclusively nitrogen. Moreover, the device include a device for heating the aforementioned objects, which can heat the objects to a temperature of at least 60° C. during treatment. A method of using the device is also described.

3 Claims, 2 Drawing Sheets

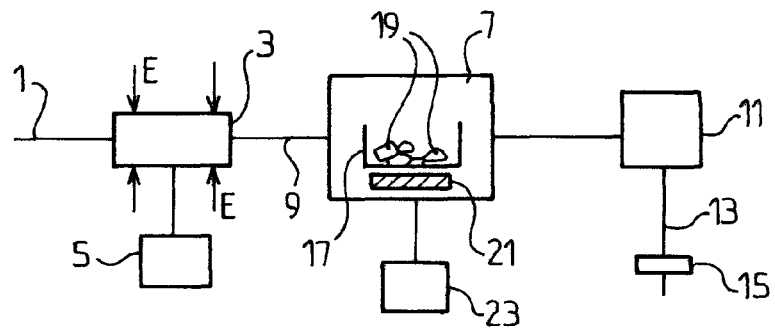
FIG.1
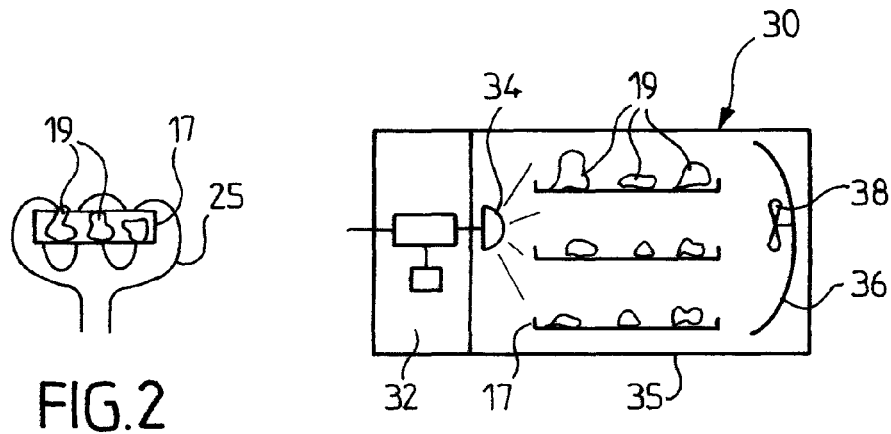
FIG.2
FIG.3
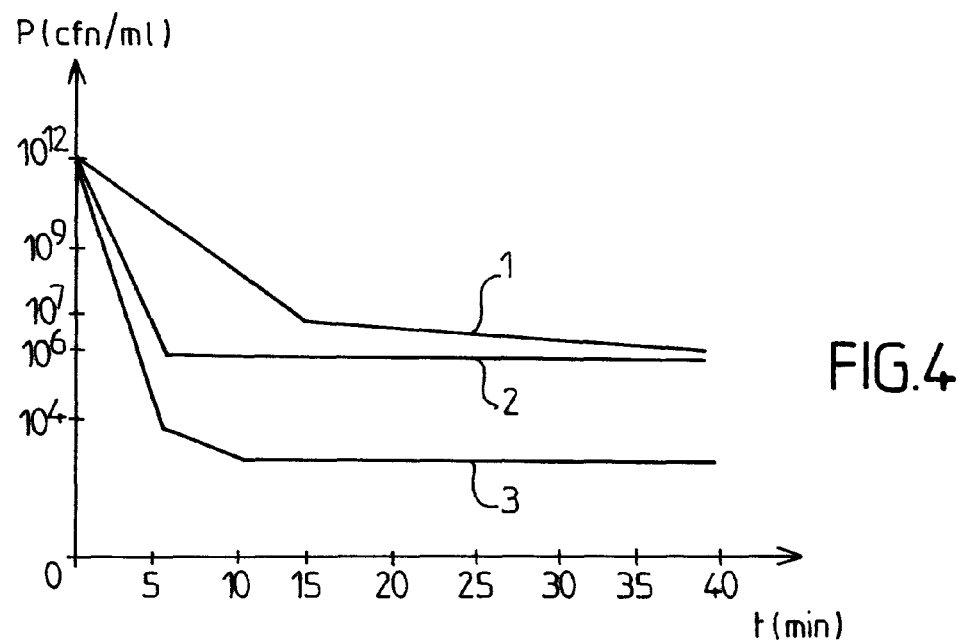
FIG.4

POST-DISCHARGE PLASMA STERILISATION DEVICE AND METHOD

The present invention relates to a sterilisation device, particularly intended for medical or surgical instruments or apparatus. It also relates to a method for using such a device.

In medical circles, sterilisation is usually obtained by means of an autoclave in which the instruments to be sterilised are taken to a determined high temperature, of the order of 120° C., and this for determined periods of time with cycles imposed by legislation. It will firstly be noted that autoclaves are limited to the sterilisation of objects of small volume, which excludes the use thereof for ensuring sterilisation, for example, of tubes of apparatus such as dialyzers or dental treatment units. Furthermore, the application of a temperature higher than 100° C. to modern surgical instruments and apparatus creates numerous servitudes and prevents, in particular, subjecting to sterilisation fragile objects or accessories which comprise for example parts made of synthetic polymer materials, which are usually particularly heat-sensitive.

This is why, during recent years, one has turned towards methods which allow sterilisations at low temperature to be effected.

Among these methods, those calling upon gaseous plasma will be more particularly retained. It will be recalled that, in these techniques, a gas, not having bactericidal properties per se, is used, which is subjected to an electric field of which the intensity is sufficiently high to provoke ionisation thereof and the dissociation of its molecules, so that a plasma is thus obtained which is constituted by ions and electrons. It has been observed that the plasma presented high bactericidal properties which have been used for ensuring sterilisation of medical and surgical instruments. To that end, the plasma thus produced is admitted in a treatment chamber where it is brought into the presence of the instruments which it is desired to sterilise.

However, it is known that, although the plasma possesses high sterilising properties, it presents the drawback of also presenting a destructive effect on certain materials such as in particular synthetic plastics materials, this excluding its use for sterilising numerous medical or surgical instruments.

It is also known that the gas produced downstream of the plasma, hereinafter designated as "post-discharge gas", presents sterilising properties. This gas which is generated at the end of the plasma is no longer subjected to the effect of the electric field, so that the electrons and the ions which constitute the plasma disappear by recombination in the gas and after diffusion on the walls of the tube.

Patent WO 00/72889 has proposed for example a method of sterilisation which employs in particular, as gas constituting the plasma, a mixture of oxygen and of nitrogen. According to this technique, it has been observed that the presence of atomic oxygen in the post-discharge gas has the effect of subjecting to the action of oxidation the polymers used in the surgical domain, whether it be question of parts of instruments such as in particular dental handpieces, ultrasound apparatus, endoscopes, catheters, joints, motors or various apparatus.

Moreover, during the formation of the gaseous plasma, the interaction of the atomic oxygen and of the atomic nitrogen has the effect of producing an ultraviolet radiation whose bactericidal action is added to the effect of the post-discharge gas itself. However, although this function of sterilisation produced by the ultraviolet is advantageous in that it improves the power of sterilisation of the device, it presents a serious drawback in that the effects of the ultraviolet rays add to the aggressive nature of the treatment.

The present invention has for its object to overcome the afore-mentioned drawbacks by proposing a low-temperature sterilisation device employing a plasma allowing any emission of oxygen and of ultraviolet rays in the course of treatment to be avoided, this making it possible to respect the integrity of the apparatus and accessories to be sterilised which comprise materials sensitive to the phenomena of oxidation as well as to the ultraviolet rays, and this without reducing for all that the efficiency of the device.

The present invention thus has for its object a device for sterilising objects, in particular medical or surgical instruments, of the type adapted to create from a gaseous flow subjected to an electric field a gaseous plasma of which the post-discharge flow which issues therefrom is brought into contact with the surface of the objects to be treated, characterized in that:

the gaseous flow is exclusively constituted by nitrogen,
it comprises means for heating said objects adapted to take the latter, in the course of treatment, to a temperature of at least 60° C.

The post-discharge flow which results from the gaseous plasma is preferably admitted into a sterilisation chamber in which said objects are arranged. The walls of this sterilisation chamber may be constituted by a material presenting a low capacity of recombination of the nitrogen atoms, such as for example glass and/or ceramics and/or a polymer. The objects to be sterilised may be arranged on a metal object-holder whose nature will be such that, under the effect of the recombination of the nitrogen atoms, this object-holder heats up and ensures heating of the objects that it contains. This object-holder, which may in particular be made of brass, may also be provided with its own heating means.

The electric field will preferably be produced by a microwave generator, but it may also be so by direct or pulsating current discharges or by radio-frequencies.

In an embodiment of the invention, the sterilisation chamber may be constituted by an autoclave and this autoclave may constitute the means for heating the instruments to be sterilised.

Furthermore, the means adapted to generate the plasma may be contained in the door of the autoclave.

In a variant embodiment of the invention, heating of the objects contained in the sterilisation chamber will be ensured at least in part by the walls of the latter which, to that end, will be constituted by a material adapted to heat up by recombination of the nitrogen atoms. Heating of the objects may also be ensured by providing the walls of the sterilisation chamber with additional heating means, particularly electric ones.

The present invention is particularly advantageous in that it makes it possible to ensure sterilisation of the tubes and internal cavities of apparatus and even of apparatus of large volume such as for example dental treatment units, dialysis apparatus, etc. . . . To that end, post-discharge flow will be injected via an orifice in this apparatus, through the tubes and internal cavities of the latter, which flow will be extracted, for example by suction via another of its orifices.

For certain apparatus of smaller dimensions and which are capable of being placed in a treatment chamber, the post-discharge flow may be conducted both in the treatment chamber and in the apparatus via an orifice of the latter and it may be extracted, for example by suction, both from the treatment chamber and from the apparatus via a second orifice.

The present invention also has for its object a method for sterilising objects, in particular medical or surgical instruments, in which a plasma is created by action of an electric field on a gaseous flow and the post-discharge flow resulting therefrom is brought into contact with the surface of the objects to be treated, characterized in that:

nitrogen is exclusively used as gaseous flow, the objects to be treated are heated to a temperature of at least 60° C.

According to the invention, it is possible to raise the temperature of the instruments during the treatment, such increase in temperature being able to be obtained by heating the object-holder, or by heating the sterilisation chamber, but also by recombination of the atoms of the post-discharge gas on the surfaces of the object-holder and/or of the sterilisation chamber.

In effect, it is known that the nitrogen atoms produced by the post-discharge of pure nitrogen, react together, by atomic recombination on the surface of the objects to be treated, and that these reactions are exothermic. It has thus been established that, under the experimental conditions tested, namely: a pressure of 665 Pa, a micro-wave generator power of 100 W and a flowrate of 1 l/min, the surface temperature of the materials attained 80° C. for brass, 55° C. for steel, 60° C. for aluminium, 55° C. for titanium, 40° C. for ceramics and 37° C. for glass.

Now, it has been established, in the case of the bacterium *Escherichia Coli*, that a temperature of 60° C. was necessary to induce a decrease in the bacterial population by $10^6$ in 40 minutes of exposure to the post-discharge of nitrogen. In this way, in order to ensure an efficient sterilisation of the instruments whatever their nature, it is necessary to take their surface to a minimum temperature of 60° C. in the course of the sterilisation.

Furthermore, according to the invention, by employing a gas flow constituted exclusively of nitrogen, the formation of ultraviolet rays during the production of the plasma is avoided, which rays have the effect of being detrimental to the integrity of the synthetic materials used most of the time in the surgical instruments or accessories.

A form of embodiment of the present invention will be described hereinafter by way of non-limiting example, with reference to the accompanying drawing, in which:

FIG. 1 is a schematic view of a sterilisation device according to the invention.

FIG. 2 is a variant embodiment of the sterilisation device shown in FIG. 1.

FIG. 3 is a schematic view of a variant embodiment of the device according to the invention.

FIG. 4 is a diagram showing the bacterial decrease of *E. Coli* as a function of the sterilisation time, and this for different values of temperature of heating of an instrument-holder.

Figure 5:
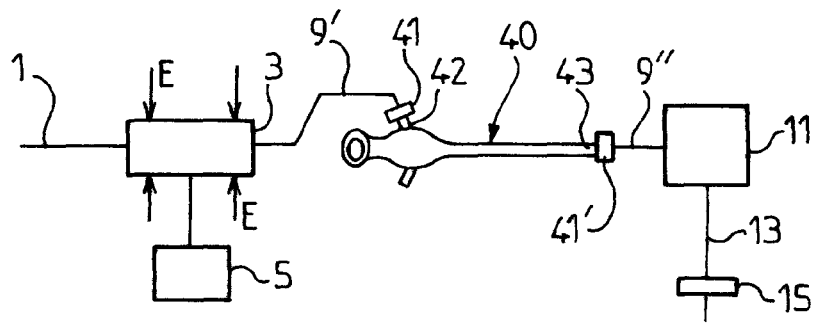
FIGS. 5 and 6 are schematic views of two applications of the device according to the invention to the sterilisation of the tubes and internal cavities of an endoscope and of a fibroscope.

FIG. 1 very schematically shows a sterilisation device according to the invention employing gaseous plasma. This device comprises a conduit 1 for admission of a nitrogen flow which traverses an enclosure in vacuo subjected to the action of an electric field generator constituted by a generator 3 of micro-waves at 2.45 GHz, whose power is regulated by control means 5. The post-discharge gas generated by the plasma thus produced (in known manner) is conducted into a treatment chamber 7 via a conduit 9. This treatment chamber 7 is disposed in the post-discharge zone of the plasma and is in communication with a vacuum pump 11. The latter entrains the post-discharge gas in the treatment chamber 7 and ensures evacuation of the gases towards the outside via a conduit 13 provided with the appropriate filters 15.

The treatment chamber 7 comprises a metal object-holder 17 which is intended to receive the objects 19 which it is desired to sterilise.

The object-holder 17 is provided with heating means 21 whose temperature is controlled by a control device 23. These heating means may in particular be constituted by an electrical resistor or, as shown in FIG. 2, by induction heating means 25.

As shown in FIG. 3, the treatment chamber may be constituted by an autoclave of the type such as those used to ensure sterilisation of medical or surgical instruments.

In this Figure, the autoclave 30 is thus constituted by an enclosure 35, of substantially parallelepipedic shape which is closed on one of its sides by a pivoting door 32. This pivoting door is sufficiently thick to contain the various elements necessary for generating the plasma. It comprises, on its front face, a nozzle 34 for exit of the post-discharge gas, intended to supply the interior of the enclosure. This nozzle 34 may advantageously terminate in one or more injectors making it possible, in particular, to homogenise the flow of the post-discharge gas.

In the form of embodiment shown in FIG. 3, the enclosure 35 is provided on its wall opposite the door 32 with a "reflector" 36 and with a fan 38 which contributes to the homogenisation of the post-discharge gas in the enclosure 35. Such an arrangement is interesting in that it allows the user to have available a multi-function autoclave, namely a conventional function of autoclave and a function in which sterilisation is effected by post-discharge gas and at low temperature. In this way, depending on the objects to be sterilised, the user will have the possibility of employing the most appropriate mode of sterilisation.

In this variant embodiment of the invention, the autoclave may be used to take the objects to be sterilised to the desired temperature.

In effect, it has been observed that a post-discharge gas presenting bactericidal properties could be obtained from a gaseous supply flow constituted exclusively of nitrogen without for all that calling upon atomic oxygen, as is taught by the prior state of the art.

It has been established that a post-discharge gas obtained from a gaseous flow constituted exclusively of nitrogen had a marked biocidal effect on the bacteria.

It has also been observed that the magnitude of the biocidal effect obtained was connected with the nature of the object-holder used and with the temperature to which the latter was taken in the course of the sterilisation operation.

For example, there was disposed in an instrument-holder made of steel comprising electrical heating means of the type shown in FIG. 1, a bacterial population of *Escherichia Coli* which was subjected to the action of a post-discharge gas obtained from a flow of pure nitrogen under a pressure of 6 hPa.

The instrument-holder was heated to temperatures of 60° C., 80° C. and 120° and the remaining bacterial population was measured after five, ten, fifteen and forty minutes, respectively. The corresponding curves of FIG. 4 represent the variation of colonies of bacteria per ml as a function of time.

The following results will be retained in particular therefrom:

| Curve No. | Temp instrument-Holder (° C.) | Duration | Coefficient of decrease |
|---|---|---|---|
| 1 | 60 | 15 mins. | $10^5$ |
|   | 60 | 40 mins. | $10^6$ |
| 2 | 80 | 5 mins. | $10^6$ |
| 3 | 120 | 5 mins. | $10^8$ |

It is thus observed that the present invention allows, as a function of the level of temperature which it is possible to apply to an object to be sterilised without degrading it, the mode of sterilisation which is applicable thereto to be selected. Thus, if the object in question is capable of withstanding a temperature of 120° C., it may be subjected to a particularly rapid treatment, since the latter only lasts 5 mins., heating the object-holder to 120° C. The bacterial population will in that case be reduced by $10^8$.

For a more fragile object, which cannot withstand temperatures higher than 80° C., the object-holder will be heated to that temperature and the treatment will then likewise last 5 mins., the coefficient of reduction of the bacterial population in that case being $10^6$. However, it is known that, in the matter of sterilisation of medical or surgical instruments, a sterilisation time of 40 mins. is quite acceptable having regard to the conventional known techniques, and the preceding measures show that, at the end of this time, a decrease in the bacterial population of $10^6$ is obtained at a temperature of 60° C., which is particularly high-performance.

Finally, in the cases where a decrease in the bacterial population of $10^5$ is sufficient and where it is desired to employ a shorter time, if the object to be sterilised is particularly fragile, the object-holder will be heated to a temperature of 60° C. and a treatment time of 15 mins. will be applied.

The present invention also makes it possible to ensure the sterilisation of parts of apparatus which, by reason of their nature, or of their dimensions, cannot be sterilised in sterilisers of conventional type.

As shown in FIG. 5, the sterilisation device shown in FIG. 1 has thus been applied to the sterilisation of an endoscope 40. To that end, an inlet 42 thereof is connected by means of a connector 41 to a conduit 9' connected to the outlet of the plasma generator 3, so that the post-discharge gas is formed inside a sterilisation chamber constituted by the tubes and internal cavities of the endoscope 40. The outlet 43 of the latter is similarly connected, via a connector 41', to a conduit 9" connected to a vacuum pump 11. According to the invention, the post-discharge gas which passes through the interior of the cavities of the endoscope will ensure sterilisation of the latter.

It will be noted that such a mode of use is particularly interesting, on the one hand, concerning its easy use by the practitioner and, on the other hand, in that it makes it possible to ensure sterilisation of apparatus which may comprise on their outer surface parts made of materials which cannot withstand the temperatures required by the sterilisations of conventional type.

Figure 6:
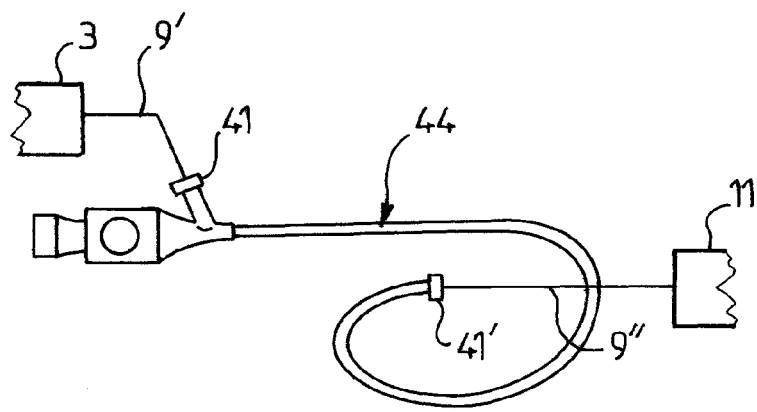

As shown in FIG. 6, an identical sterilisation device may also be applied to other apparatus and, in particular, to a fibroscope 44.

Figure 7:
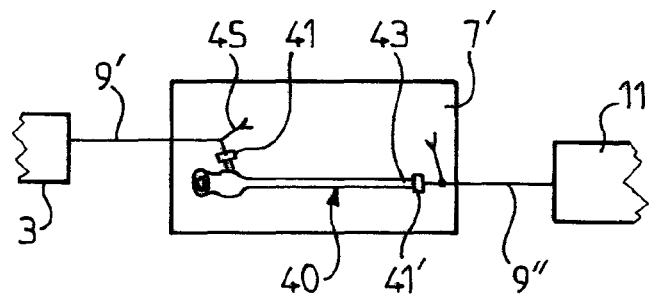
FIG. 7 is a schematic view of an example of sterilisation of the outer surface and of the tubes and internal cavities of an apparatus.

Of course, it is also possible according to the invention to ensure sterilisation of the whole of the apparatus, i.e. its tubes and internal cavities as well as its outer surface, when this is desired, by placing it inside a sterilisation chamber 7' which is in communication via conduit 9' with the plasma generator 3, this conduit being connected to an inlet of the endoscope by a connector 41 and also being in communication by a nozzle 45 with the interior of the sterilisation chamber 7' in which the post-discharge gas is formed, the outlet 43 of the endoscope 40 as well as the internal volume of the sterilisation chamber being connected to a vacuum pump 11 as shown in FIG. 7.

The device according to the invention may also be used for ensuring sterilisation of the tubes and internal volumes of a dental treatment unit by connecting an inlet of the pipes of this unit to the admission of the post-discharge gas, and the outlet thereof to a vacuum pump.

Figure 8:
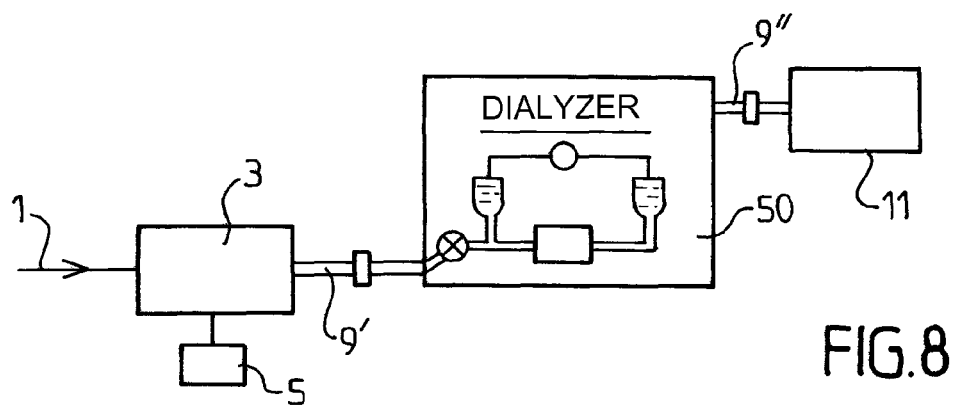
FIG. 8 is a schematic view of an application of the device according to the invention to the sterilisation of the tubes and internal cavities of a dialysis apparatus.

Another particularly interesting application of the invention consists in the sterilisation of dialysis apparatus, as shown in FIG. 8. The dialysis apparatus 50 is thus connected by its inlet to a conduit 9' for admission of the post-discharge gas and its outlet is connected to a vacuum pump 11.

The invention claimed is:

1. Device for sterilizing objects, the device being adapted to create from a gaseous flow subjected to an electric field a gaseous plasma of which a post-discharge flow which issues therefrom is brought into contact with a surface of the objects to be treated, the device comprising:

a sterilization chamber having therein a metal object holder on which the objects to be sterilized are disposed, wherein walls of said sterilization chamber comprise a material that is adapted to heat up by recombination of nitrogen and have a capacity of recombination of nitrogen less than that of said metal object holder; and means for producing said plasma from a gaseous flow exclusively constituted by nitrogen, said means for producing including an enclosure in which the gaseous plasma is produced, said enclosure comprising a generator of microwaves and being connected to said sterilization chamber by a conduit, the post-discharge flow that issues from the gaseous plasma being admitted via said conduit into said sterilization chamber, wherein said metal object holder and the walls heat under the effect of recombination of the nitrogen and heat the objects on said metal object holder to at least 60° C.

2. Device according to claim 1, wherein said sterilization chamber is an autoclave.

3. Device according to claim 1, wherein said metal object holder is made of brass.

\* \* \* \* \*